US00PP13055P2

(12) United States Plant Patent
Saville

(10) Patent No.: US PP13,055 P2
(45) Date of Patent: Oct. 8, 2002

(54) MINIATURE ROSE PLANT NAMED 'SAVAPPLE'

(75) Inventor: John Saville, Newburyport, MA (US)

(73) Assignee: Nor"East Miniature Roses, Inc., Rowley, MA (US)

( * ) Notice: Subject to any disclaimer, the term of this patent is extended or adjusted under 35 U.S.C. 154(b) by 51 days.

(21) Appl. No.: 09/727,065

(22) Filed: Nov. 30, 2000

(51) Int. Cl.[7] ..... A01H 5/00

(52) U.S. Cl. ..... Plt./122

(58) Field of Search ..... Plt./116, 120, 121, Plt./122

*Primary Examiner*—Howard J. Locker

(57) ABSTRACT

'SAVapple' is a new and distinct variety of miniature rose plant primarily identified by its small coral flowers borne on a low growing, well branched, compact and mounding plant. Buds and flowers with good form can be found on the plant continuously during the growing season and well into the fall. The glossy foliage has very good disease resistance.

1 Drawing Sheet

GENUS/SPECIES AND VARIETAL DENOMINATION OF THE PLANT

Genus/species: *Rosa chinensis 'minima'*.
Varietal denomination: 'SAVapple'.

BACKGROUND OF THE INVENTION

This present invention relates to a new and distinct variety of hardy, bush type plant of the miniature rose class, with similarities to 'MEIgali'(formerly U.S. Plant Pat. No. 2,646, also listed as 'MEIgabi' and sold and marketed as Starina). The buds and flowers of this new invention are similar in form but slightly larger in size than those of 'MEIgali', and the two plants are of a similar color but with the new invention being a softer shade of a coral red. Another notable difference is length of blooming season with this new invention bearing flowers longer into the fall than 'MEIgali' and holding it's form better in cool and low light conditions.

The flowers of this new invention are also lighter and more coral in color than its pollen parent, 'SAVaspark' (U.S. Plant Pat. No. 9,799) a scarlet red miniature.

This present invention is a new and distinct variety of miniature rose plant created in a greenhouse in Rowley, Mass., under conditions of careful control and observation, by crossing the following two rose plants:

The seed parent is 'MORsegold' (U.S. Plant Pat. No. 6,617), a prolific miniature rose, with medium yellow flowers.

The pollen parent is 'SAVaspark' (U.S. Plant Pat. No. 9,799) a scarlet red miniature.

The present invention relates to a new and distinct variety of hardy, dwarf, bush type rose plant of the miniature class (*Rosa chinensis 'minima'*). This invention can be grown quite satisfactorily, in a greenhouse, outside in containers or as a garden perennial, with protection recommended through the winter in severe climates. The varietal denomination of this new rose is 'SAVapple'.

Asexual reproduction by cuttings of this new variety in Essex County, Mass. shows that all distinguishing characteristics of this rose continually come true to form.

SUMMARY OF THE INVENTION

The present invention relates to a new and distinct variety of miniature rose plant being primarily characterized — as to novelty — by its small coral blooms and glossy, disease resistant foliage.

The variety is further characterized by:

An abundance of these small flowers and always at least a few on the plant during it's growing season and late into the fall.

A plant which has good vigor, is upright, well branched and compact, forming a small mound with abundant medium green, glossy foliage.

BRIEF DESCRIPTION OF THE DRAWING

The accompanying color photograph show specimens of the flower of this new variety in different stages of development as grown and observed in September, under plastic in Essex County, Mass.

BOTANICAL DESCRIPTION OF THE PLANT

Following is a detailed description in outline form pertaining specifically to this new and distinct variety of miniature rose plant when grown and observed in September, under plastic in Essex County, Mass. All major color plate identifications made are referring to The Royal Horticulture Society Chart except where common terms of color definition are employed.

FLOWERS

Class: Miniature rose.
Blooming habit: Continuous, late into the fall.
Bud:
- *Size.*—Small.
- *Form.*—Ovate.
- *Color.*—When sepals first divide — a dark coral red, near 43A.
- *Sepals.*—Color — a medium yellow green, near 144A. Characteristics — lanceolate with occasional foliation, extending just beyond the tip of the bud, and only remaining attached until petals drop.

*Peduncle.*—Length — averaging 1 to 1¼ inches. Aspect — straight. Strength — erect. Color — slightly lighter than the sepals, a medium yellow green, between 144A and 144B.

Bloom:

*Size.*—When fully expanded — 1½ inches.

*Form.*—High centered at first, becoming flat; petals remain loosely rolled outward.

*Petalage.*—20 to 25.

*Petaloids.*—0 to as many as 7.

*Fragrance.*—Slight.

*Lastingness of the bloom.*—About 5–8 days on the plant; lastingness as a cut flower has not been systematically observed.

Petals:

*Texture.*—Medium thick.

*Appearance.*—Inside — velvety, outside — satiny.

*Form.*—Very wide spatulate.

*Arrangement.*—Arranged shingle-like.

*Color.*—During the first few days — a medium coral red, between 43B and 44C and the reverse being a more pink shade of a medium red, between 51D & 48D, and becoming a light orange yellow, near 23D, at the base. As the bloom ages it gradually becomes lighter and more pink, finishing with a mix of near 180D and 51D (both surfaces), and the bloom opens to show some very light yellow near the base of the petals.

*General tonality.*—Medium coral red.

REPRODUCTIVE ORGANS

Stamens, filaments and anthers:

*Arrangement.*—Regularly arranged around styles.

*Quantity.*—Ample.

*Filaments.*—Length — near non-existent to ⅛ inch with the shortest being near the styles. General color — same as anthers, a light lemon yellow.

*Anthers.*—Color — filaments and anthers being the same coloring, a light lemon yellow, near 13D.

Pollen:

*Color.*—Dark yellow, near 17B.

*Quantity.*—Very little.

Pistils, styles and stigmas:

*Quantity.*—Many.

*Styles.*—Thin, tight together, slightly uneven length, about 1/16 inch.

*Stigmas.*—Stigmas and styles are the same coloring of a pale and very light celery green, near 145D.

Hips: None observed.

PLANT

Habit: Upright but spreading to form a small mound.

Growth: Vigorous and well branched, maturing at 14 to 16 inches in height and only spreading to about 12 inches.

Foliage:

*Size.*—Medium.

*Quantity.*—Abundant.

*Color.*—New foliage — dark green on the upper surface, near 137A, and a medium green on the underside, near 147B. Older foliage — a dark green, between 147A and 146A, on the upper surface and a medium green, near 147B, on the reverse.

*Texture.*—Glossy on the upper surface and matte on the underside.

*Leaflets.*—Usually 5 leaflets, but also may have 3 or 7. shape — oval, pointed. edge — fine, even serration.

*Leaf stem.*—Smooth and the same shade of a medium green as the underside of the new foliage, near 147B, and the underside of the leaf stem being a lighter and olive green, near 146B.

*Stipules.*—Slightly bearded, averaging 7/16 inches in length.

Disease resistance: Very good resistance to black spot and downy mildew, no rust observed.

Wood: Smooth with new wood being a medium yellow green, between 144A and 146A, and old wood is a medium green, near 147B.

Thorns:

*Quantity on main stalks and laterals.*—Ordinary.

*Form.*—A flat base tapering to a fine point, thin, straight and being slightly angled downward, and being of medium length.

*Color when young.*—A pale yellow green flushed with light coral.

Winter hardiness: Needs protection in cold climates.

The following is claimed:

1. A new and distinct variety of hardy miniature rose plant substantially as illustrated and described, characterized by small coral buds and flowers on a plant of upright and mounding growth habit, and flowering late into the fall.

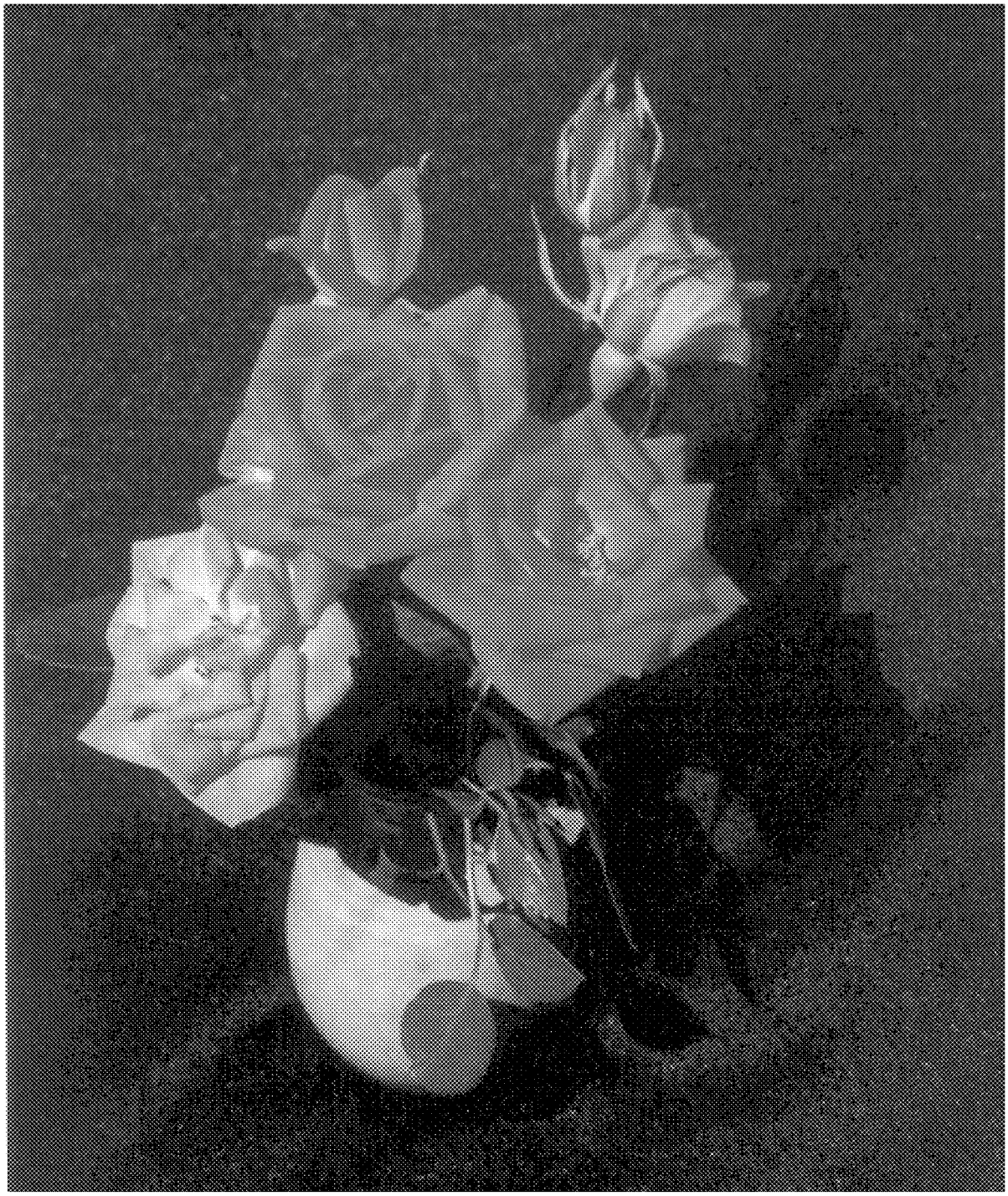

* * * * *